(12) United States Patent
Rad

(10) Patent No.: US 8,663,176 B2
(45) Date of Patent: Mar. 4, 2014

(54) CHEMICAL APPLICATOR

(75) Inventor: Omid Rad, Toorak Garderis (AU)

(73) Assignee: Ariana Holdings Pty Ltd, Adelaide, S.A. (AU)

( * ) Notice: Subject to any disclaimer, the term of this patent is extended or adjusted under 35 U.S.C. 154(b) by 747 days.

(21) Appl. No.: 12/097,325

(22) PCT Filed: Dec. 13, 2006

(86) PCT No.: PCT/AU2006/001887
§ 371 (c)(1),
(2), (4) Date: Jun. 20, 2008

(87) PCT Pub. No.: WO2007/068045
PCT Pub. Date: Jun. 21, 2007

(65) Prior Publication Data
US 2008/0312635 A1    Dec. 18, 2008

(30) Foreign Application Priority Data
Dec. 14, 2005    (AU) ................................ 2005907011

(51) Int. Cl.
*A61M 5/32*    (2006.01)
(52) U.S. Cl.
USPC ....................................... 604/272; 604/99.02
(58) Field of Classification Search
USPC ............... 604/174, 164.12, 166.01, 136, 181, 604/272; 606/185
See application file for complete search history.

(56) References Cited

U.S. PATENT DOCUMENTS

| 1,960,738 | A | | 5/1934 | Giezentanner | |
| 2,237,447 | A | | 4/1941 | Rea | |
| 2,687,598 | A | | 8/1954 | Calhoun | |
| 3,991,627 | A | * | 11/1976 | Laird et al. | 73/864.16 |
| 4,357,779 | A | | 11/1982 | Maddock | |
| 4,403,881 | A | | 9/1983 | Keeton | |
| 4,488,550 | A | * | 12/1984 | Niemeijer | 606/116 |
| 4,716,677 | A | | 1/1988 | Moore | |
| 5,724,765 | A | | 3/1998 | Wegner | |
| 6,612,262 | B2 | * | 9/2003 | Julien et al. | 119/712 |
| 6,656,147 | B1 | | 12/2003 | Gertsek et al. | |
| 6,780,171 | B2 | * | 8/2004 | Gabel et al. | 604/181 |
| 6,881,203 | B2 | | 4/2005 | Delmore et al. | |
| 2005/0226922 | A1 | * | 10/2005 | Ameri et al. | 424/449 |
| 2005/0251095 | A1 | | 11/2005 | Giap | |

FOREIGN PATENT DOCUMENTS

| CN | 1415385 A | 5/2003 |
| DE | 202006009246 U1 | 8/2006 |
| GB | 189416075 | 8/1985 |
| GB | 2384158 A | 7/2003 |
| WO | 2004030726 A1 | 4/2004 |

OTHER PUBLICATIONS

L. Tang, et al., Color Image Segmentation With Genetic Algorithm for In-Field Weed Sensing, ASAE 42(6): 1897-1910, 1999.

* cited by examiner

*Primary Examiner* — Kevin C Sirmons
*Assistant Examiner* — Brandy S Lee
(74) *Attorney, Agent, or Firm* — Levine Mandelbaum PLLC

(57) ABSTRACT

A device and method for applying chemicals to internal tissue of living organisms, including the internal tissue of plants and animals, which organisms reside in mediums such as land, air or water. Piercing elements are engageable with a chemical reservoir in order to coat of the piercing elements with a chemical. Once coated, the piercing elements are used to pierce a living organism's tissue, such as plant tissue, to deliver the chemical.

15 Claims, 5 Drawing Sheets

CHEMICAL APPLICATOR

FIELD OF THE INVENTION

The present invention relates to the field of chemical applicators and, specifically to the subfield of chemical applicators which incorporate chemical application devices and methods for applying chemicals to the internal tissue of living organisms, including the internal tissue of plants and animals which may reside in media including air, land and/or water. The chemical applicator device and method is designed to increase the effectiveness of chemicals applied to the body tissues of target organisms, improving the effectiveness of the chemicals at lower doses than achieved with conventional devices and methods of application, whilst minimising exposure of non-target animals or plants to the chemical; however, the invention is not restricted to this particular field of use.

BACKGROUND OF THE INVENTION

Methods and devices for applying chemicals, such as herbicides and fertilisers, to plants are known. Such methods and devices include spraying and direct application methods and devices.

It is known that spraying-based methods may be suitable when large areas of target plants are involved. However, spraying methods may be unsuitable where target plants are interspersed with non-target plants. In this case, spraying-based methods of herbicide application may not be sufficiently accurate to apply a herbicide only to the target plants. This may result in damage of nearby non-target plants and contamination of the target plant environs.

Furthermore, spraying methods may also not be suitable under particular environmental conditions such as high wind or rain. Under these conditions, the herbicide may be either dispersed or diluted such that the concentration is not sufficient to be effective on the target plants and/or the herbicide may wash off or drift onto non-target plants and cause damage.

In light of the problems associated with spraying-based methods, a number of direct-application or contact type chemical applicator technologies have been developed in various attempts to address these problems.

For example, U.S. Pat. No. 4,357,779, to M. E. Maddock, describes a chemical applicator comprising a sponge applicator connected to a chemical reservoir wherein flow of chemical from the reservoir to the sponge applicator is controlled by a flow control valve.

U.S. Pat. No. 4,403,881, to J. H. Keeton, describes a hollow handled chemical applicator which comprises a chemical reservoir within the upper part of the handle. Chemical from the reservoir is supplied in discrete doses to a sponge applicator at the lower end of the device through a slit valve, which is openable in response to the operation of a button by a user of the device.

U.S. Pat. No. 4,716,677, to J. E Moore, describes a hand-held chemical applicator comprising a chemical applicator pad mounted between pincers or tweezers. The pincers or tweezers may then be used to grip a plant and thereby apply the herbicide to the surface of the plant gripped by the pincers.

Each of the herbicide applicators described above uses a sponge or absorbent pad to apply chemical to the surface of a plant. As such, the chemical is subject to wash-off during rainfall. This wash-off potentially leads to exposure of non-target plants or animals to the chemical and/or unnecessary contamination of the environment with the chemical.

Furthermore, wash-off potentially:
1. exposes non-target plants and animals to the chemical; and
2. reduces the concentration of the chemical on the target plant surface. This potentially reduces the effective dose of the chemical delivered to the target plant. The reduced effective dose of the chemical on the target plant surface may then necessitate repeat applications of the chemical and/or application of the chemical at a higher concentration. As would be appreciated, this potentially compounds the problems associated with chemical wash-off and increases the potential for non-target plant and animal exposure to the chemical.

U.S. Pat. No. 5,724,765, to W. A. Wegner, describes a herbicide applicator comprising a pair of opposable jaws, each comprising an absorbent pad and a plurality of needles extending from each jaw into the pad. This device also comprises a herbicide reservoir which is connected by conduit to the absorbent pad on each jaw. When a plant is grasped by the jaws, the needles penetrate the surface of a plant. In this way, the herbicide, which is applied to the absorbent pads, coats the surface of the plant and then flows into holes produced in the plant tissue by the needles.

The device described in the Wegner patent does potentially lead to more effective utilization of herbicide, as wounding of the plant allows herbicide, from herbicide absorbent pads, to infiltrate the internal tissues of the plant. However, with the Wegner device, a significant amount of herbicide is still applied to the surface of the plant, via the absorbent pads. This surface-applied chemical is still prone to wash-off and thus can lead to exposure of non-target plants and animals to the chemical.

Methods for applying chemicals, such as pharmaceuticals, to animals are known. Such methods include injecting methods where a syringe is used to allow a pharmaceutical to directly flow from the syringe's reservoir down the barrel of a needle into the target tissue. It is also well known that injectable darts are used, which are based on the syringe technology.

Injecting methods may be suitable when a small number of specific target animals require an injectable pharmaceutical and when the target animal is accessible or lives in accessible media such as on land. However, injecting methods may be unsuitable where target animals are numerous, fast moving, interspersed with non-target plants and animals, remotely located, live in a medium such as below water or are out of reach and fast moving. In this case, injecting-based methods of pharmaceuticals may not be suitable for delivering the pharmaceutical to the target animals in an efficient and timely manner. Likewise, in situations where a large number of animals require specific doses of a pharmaceutical to be administered in a sterile manner, the syringe-style application devices have considerable limitations.

In light of the problems associated with injecting-based methods and devices, a number of direct-application or contact type chemical applicators have been developed in various attempts to address these problems.

For example, Patent Publication No. CN1415385 describes a miniature needle array sheet which supplies the pharmaceutical via said minipore array into the skin. Such devices can take the form of a transdermal patch to apply the pharmaceutical; however, such method and devices have limitations of applying pharmaceuticals to birds or water based animals, each patch has only a single use and used patches contribute to potentially toxic waste material within the environs when the patch is no longer attached to the target animal.

To overcome the deficiencies of, or to provide an alternative to, existing chemical methods and devices, the present invention provides a chemical applicator which substantially specifically delivers a chemical to the Internal tissues of the living organism in this way, chemical coating of the surface of organisms would be minimized and thereby the potential for wash-off of the chemical, and subsequent exposure of non-target plants or animals would also be reduced Substantially specific application of a chemical to the internal tissues of an organism would also potentially increase the effective utilization of a chemical, as the chemical could be delivered to the internal tissues of the organism where it is most effective, thus potentially decreasing the amount and/or concentration of a given chemical needed to achieve a desired outcome. Further, the application method can be rapidly reused to deliver the desired chemical to numerous organisms without the necessity to re-prime or re-sterilise the piercing elements.

Before turning to a summary of the invention, it must be appreciated that the above description of the prior art has been provided merely as background to explain the context of the invention. Accordingly, reference to any prior art in this specification is not, and should not be taken as, an acknowledgment or any form of suggestion that this prior art forms part of the common general knowledge in any country.

SUMMARY OF THE INVENTION

One of the objects of the present invention is to provide a chemical applicator which uses a chemical application device and method for applying chemicals to the internal tissues living organisms, including the internal tissue of plants and animals which may reside in media such as air, or on or under water without contaminating the surrounding environment or non-target organisms.

The present invention provides a device for applying a chemical to a living organism, the device including:

a) one or more piercing elements for piercing the living organism and introducing the chemical into the living organism; and b) a chemical reservoir for containing the chemical;

wherein the one or more of the piercing elements are engageable with one or more reservoirs such that the chemical is substantially specifically applied onto one or more of the piercing elements.

The present invention may be used to deliver any chemical to a plant, animal or other living organism. Exemplary chemicals include, for example, herbicides, fungicides, growth regulators, fertilizers, genetic material, drugs, hormones, pheromones and other materials and the like which have an effect with inter- and intracellular administration to a living organism. However, in a preferred embodiment, the device of the present invention may be used to deliver a herbicide to a plant.

It would be appreciated that the living organism's surface to be pierced is dependent on factors including:

1. chemical type,
2: application surface, and
3. access to the living organism's tissue to which the chemical is applied.

Chemical can be applied to animals, plants or other living organisms including lichen mosses or other animal species.

The device of the present invention is predicated, in part, on the piercing elements being engageable with the chemical reservoir in order to effect the coating of the piercing elements with the chemical. Once coated, these piercing elements may then be used to pierce living organism such as plant tissue and deliver the chemical to the internal tissues of the plant.

In a preferred embodiment, engagement of the one or more piercing elements with the chemical reservoir effects substantially specific application of the chemical onto the one or more piercing elements.

In this embodiment, because only the piercing elements are coated with the chemical, very little or substantially no chemical is applied to the surface of the living organism's tissue during delivery. In this way, the potential for wash-off of the chemical is reduced and substantially all of the chemical applied to the living organism is delivered to the internal tissues of the living organism, where it is likely to be of the greatest effectiveness.

In a further preferred embodiment, the chemical reservoir comprises a body which is normally sealed to encapsulate the chemical contained within the chemical reservoir. The chemical contained within the chemical reservoir may be any suitable type of formulation. For example, solid, liquid, Suspension, paste or gel formulations are contemplated as being suitable for use in accordance with the present invention. Preferably still, the body is substantially impermeable to the chemical contained within the chemical reservoir.

More preferably, the piercing elements are disposed within the chemical reservoir, such that one or more piercing elements are normally coated with the chemical. Further preferably, retraction of one or more of said piercing elements from said chemical reservoir's surface effects re-sealing of said chemical reservoir. Still preferably, the piercing elements are chemically recoated on re-entry into the reservoir Preferably, the body includes a cartridge which is preloaded with the chemical. The preloaded cartridge is disposable. This preloaded cartridge overcomes problem relating to the filling and the re-filling of herbicide containers with poisonous herbicides by unaware consumers.

In a more preferred embodiment, the chemical reservoir includes one or more valves which are openable in response to the engagement of one or more piercing elements. The valves may be of any type. Furthermore, the valves are preferably biased to a closed position to seal the chemical reservoir when the piercing elements are not engaged. Preferably still, the seal is created in the chemical reservoir when one or more piercing elements sealingly engage with the valves.

Further preferably, the piercing elements are cleansed on entering the valves into the chemical reservoir. More preferably, the piercing elements emerge from the chemical reservoir via the valves with a chemical coating. Still preferably, the piercing elements are re-cleansed on re-entering the valves into the chemical reservoir.

Preferably, the piercing elements are raised from a first member which is pivotally attached to a second member which comprises the chemical reservoir. This facilitates, among other things, ready handling and use of the device. The first and second members may be attached through one or more pivot points, and these pivot points may be arranged such that the device adopts, for example, a 'scissor' type configuration wherein one or more of the pivot points are placed intermediate the ends of the first and second members, or a 'tong' type configuration wherein a pivot point is placed proximal to one end of the first and second members.

Preferably, the first and the second members include handles, wherein the handles are actuated to bring one or more piercing elements and the chemical reservoir into engagement. In use, these handle(s) may be manipulated by a user to bring the piercing elements and chemical reservoir into, and/or out of, engagement. The handle(s) may be placed anywhere along the first and second members that is compatible with the placement of the pivot points. For example, when the placement of the pivot point is such that the device adopts a 'tong' type configuration, the handle(s) pre preferably located on the first and/or second members intermediate the pivot point and the piercing elements or chemical reservoir. Alternatively, when a pivot point is placed such that the device adopts a 'scissor' configuration, the handle(s) may be located proximal to an end of each member such that the pivot point is intermediate to the handle and the piercing elements or chemical reservoir.

The engagement of the chemical reservoir against the living organism is further facilitated by engagement with the piercing elements, can initiate a secondary sealing function, reducing potential loss of chemical to the environment. While the invention will function advantageously against the prior art without such a seal under certain environmental conditions the seal will provide an even greater advantage over the prior art.

In a second form of the invention, the one or more piercing elements are disposed within the chemical reservoir, such that the one or more piercing elements are normally coated with the chemical; and wherein the one or more piercing elements may be extended outwardly from the chemical reservoir to apply the chemical to a living organism and withdrawn back into the chemical reservoir to effect re-sealing of the chemical reservoir.

Preferably, the device of the second form of the invention further includes an actuator, wherein actuation of the actuator effects extension of the piercing elements and withdrawal from the chemical reservoir. In a more preferred embodiment, the actuator includes an upright handle and actuation of the actuator comprises the application of force along the longitudinal axis of the handle.

Preferably still, the device of the second form of the invention further includes one or more gaskets which are openable in response to the engagement of one or more piercing elements. The gaskets may be of any type. Preferably also, a seal is created in the chemical reservoir when one or more piercing elements sealingly engage with the gaskets.

Further preferably, the piercing elements are cleansed on entering the gaskets into the chemical reservoir. More preferably, the piercing elements emerge from the chemical reservoir via the gaskets with a chemical coating. Still preferably, the piercing elements are re-cleansed on re-entering the gaskets into the chemical reservoir.

The present invention also provides a method of applying a chemical to a living organism, using a device with one or more piercing elements and one or more chemical reservoirs, including the steps of:
  a) containing the chemical in the chemical reservoirs;
  b) disposing the piercing elements within the chemical reservoirs;
  c) applying the chemical to the piercing elements within the reservoirs such that the piercing elements are chemically coated;
  d) emerge the chemically coated piercing elements from the reservoir;
  e) drawing the piercing elements through the living organism; and
  f) releasing the chemical from the chemically coated piercing elements into the living organism.

Preferably, in one form of the invention, the delivery of the chemical from the piercing elements to the organism occurs when the organism is interspersed between the reservoir and the piercing element which pierce's the organism's surface.

Preferably, in another form of the invention, the delivery of the chemical is undertaken when the piercing element, biased within the reservoir, is forcibly extended outwards from the reservoir into the organism.

The present invention also provides a device for applying a chemical to a plant, the device including:
  a) one or more piercing elements for piercing the plant and introducing the chemical into the plant; and
  b) a chemical reservoir for containing the chemical;
wherein the one or more of the piercing elements are engageable with one or more reservoirs such that the chemical is substantially specifically applied onto one or more of the piercing elements.

The present invention additionally provides also a method of applying a chemical to a plant, using a device with one or more piercing elements and one or more chemical reservoirs, including the steps of:
  a) containing the chemical in the chemical reservoirs;
  b) disposing the piercing elements within the chemical reservoirs;
  c) applying the chemical to the piercing elements within the reservoirs such that the piercing elements are chemically coated;
  d) emerge the chemically coated piercing elements from the reservoir;
  e) drawing the piercing elements through the plant; and
  f) releasing the chemical from the chemically coated piercing elements into the plant.

The present invention further provides also a device for applying a chemical to an animal, the device including:
  a) one or more piercing elements for piercing the animal and introducing the chemical into the animal; and
  b) a chemical reservoir for containing the chemical;
wherein the one or more of the piercing elements are engageable with one or more reservoirs such that the chemical is substantially specifically applied onto one or more of the piercing elements.

The present invention also provides also a method of applying a chemical to an animal, using a device with one or more piercing elements and one or more chemical reservoirs, including the steps of:
  a) containing the chemical in the chemical reservoirs;
  b) disposing the piercing elements within the chemical reservoirs;
  c) applying the chemical to the piercing elements within the reservoirs such that the piercing elements are chemically coated;
  d) emerge the chemically coated piercing elements from the reservoir;
  e) drawing the piercing elements through the animal; and
  f) releasing the chemical from the chemically coated piercing elements into the animal.

Throughout this specification, unless the context requires otherwise, the word "include", or variations such as "includes" or "including", will be understood to imply the inclusion of a stated element or integer or group of elements or integers but not the exclusion of any other element or integer or group of elements or integers.

BRIEF DESCRIPTION OF THE FIGURES

Having briefly described the general concepts involved with the present invention, exemplary preferred embodiments of the chemical applicator of the present invention will now be described with reference to the following figures.

DESCRIPTION OF THE PREFERRED EMBODIMENTS

It is to be understood that the following description is for the purpose of describing particular embodiments only, and is not intended to be limiting with respect to the above description.

The term "organism" and "living organism" is used to include "any living structure; such as a plant, animal, fungus or bacterium, capable of growth and reproduction" as defined by Chambers Online Reference.

It would be appreciated that the living organism's surface to be pierced is dependent on factors including:
1. chemical type, and
2. the internal tissue type to which it is applied.

Applied surfaces such as plant surfaces include any other surface contemplated including applications to lichen, mosses, and animal species.

The device of the present invention is predicated, in part, on the piercing elements being engageable with the chemical reservoir in order to effect the coating of the piercing elements with the chemical. Once coated, these piercing elements may then be used to pierce living organism's tissue such as plant tissue to deliver the chemical.

The term chemical is used to include herbicides, fungicides, growth regulators, fertilizers, genetic material, drugs/pharmaceuticals, small amino acid chains such as DNA and RNA, hormones, pheromones, viruses and any other substance contemplated which would have a beneficial effect with the inter- and intracellular administration to a living organism.

The preferred embodiments described are for use in delivering herbicides to target noxious target weeds strewn among desired plants. Therefore, the embodiments described show a plurality of chemical reservoirs and piercing elements. However, other arrangements can be envisaged by the person skilled in the art. For example, reducing the piecing elements and chemical reservoirs down to only one chemical reservoir and one accompanying piercing element would enable the preferred embodiment to be used for delivering specific chemical doses to target sea or animal life such as fish, mammals or poultry.

A device for applying a chemical to a living organism the said device including:

a) one or more piercing elements for piercing the surface of the living organism and introducing the chemical to the internal tissues of the living organism; and
b) a chemical reservoir for containing the chemical;
c) wherein the one or more of the said piercing elements are engageable with the reservoir in a manner such that chemical is substantially specifically applied onto the one or more of the said piercing elements Also, as set out above, in one preferred form of the invention, engagement of the one or more piercing elements with the chemical reservoir effects release of the chemical from the chemical reservoir substantially only onto the one or more piercing elements, and disengagement of the one or more piercing elements from the chemical reservoir effects resealing of the chemical reservoir. A particularly preferred embodiment of this form of the invention is shown in FIG. 1

In this embodiment, the chemical applicator 100 comprises a first member 110 carrying a plurality of piercing elements 120 extending outwardly therefrom. These piercing elements 120 are for piercing the surface of a living organism and introducing a chemical to the internal tissues of the living organism. The chemical applicator 100 further comprises a second member 130 which comprises a chemical reservoir 140 containing a chemical, such as a herbicide. The chemical reservoir 140 is modular and can be detached from the second member 130 to facilitate replacement of the chemical reservoir once the chemical therein has been exhausted, In this way, it is unnecessary to decant chemical into the chemical reservoir 130 from another vessel in order to use the chemical applicator 100. Thus, the chance of exposure of the user or other non-target living organisms or animals to the chemical is further reduced.

Preferably, the first Member 110 is pivotally attached to the second member 130 such that the piercing elements 120 and chemical reservoir 140 may be brought into, and/or out of, engagement.

In a particularly preferred embodiment, as shown in FIG. 1, the first member 110 and second member 130 are coupled to each other about a pivot 150. The pivot 150 allows the first member 110 and second member 130 to move with respect to each other and bring the piercing elements 120 and chemical reservoir 140 into, and/or out of, engagement. In this embodiment, the pivot is placed intermediate the ends of the first and second members 110 and 130, such that the device adopts a 'scissor' configuration.

As set out above, the first and/or second members (110, 130) preferably further comprise a handle, wherein the handle(s) may be manipulated by a user to bring the piercing elements 120 and chemical reservoir 140 into, and/or out of, engagement.

For example, with reference to the particularly preferred embodiment in FIG. 1, each of the first member 110 and second member 120 further comprise handles 160. These handles are positioned such that movement of the handles together causes the piercing elements 120 and chemical reservoir 140 to move toward each other and ultimately move into engagement with each other, and separation of the handles 160 causes the piercing elements 120 and chemical reservoir 140 to disengage and separate.

In order to apply a chemical to a living organism, the handles 160 are initially moved apart, thus separating the piercing elements 120 from the chemical reservoir 140. A target living organism is then placed between the separated piercing elements 120 and chemical reservoir 140. Once a living organism is in position, the handles 160 are moved together, thus causing the piercing elements 120 to penetrate through the living organism and ultimately engage with the chemical reservoir 140. The engagement process may also serve a secondary sealing function of reducing the exposure of the piercing elements to the environment.

As set out above, the piercing elements 120 on the first member 110 are engageable with the chemical reservoir 140 on the second member 130 to release chemical from the reservoir 140 onto the piercing elements 120.

Figure 1:
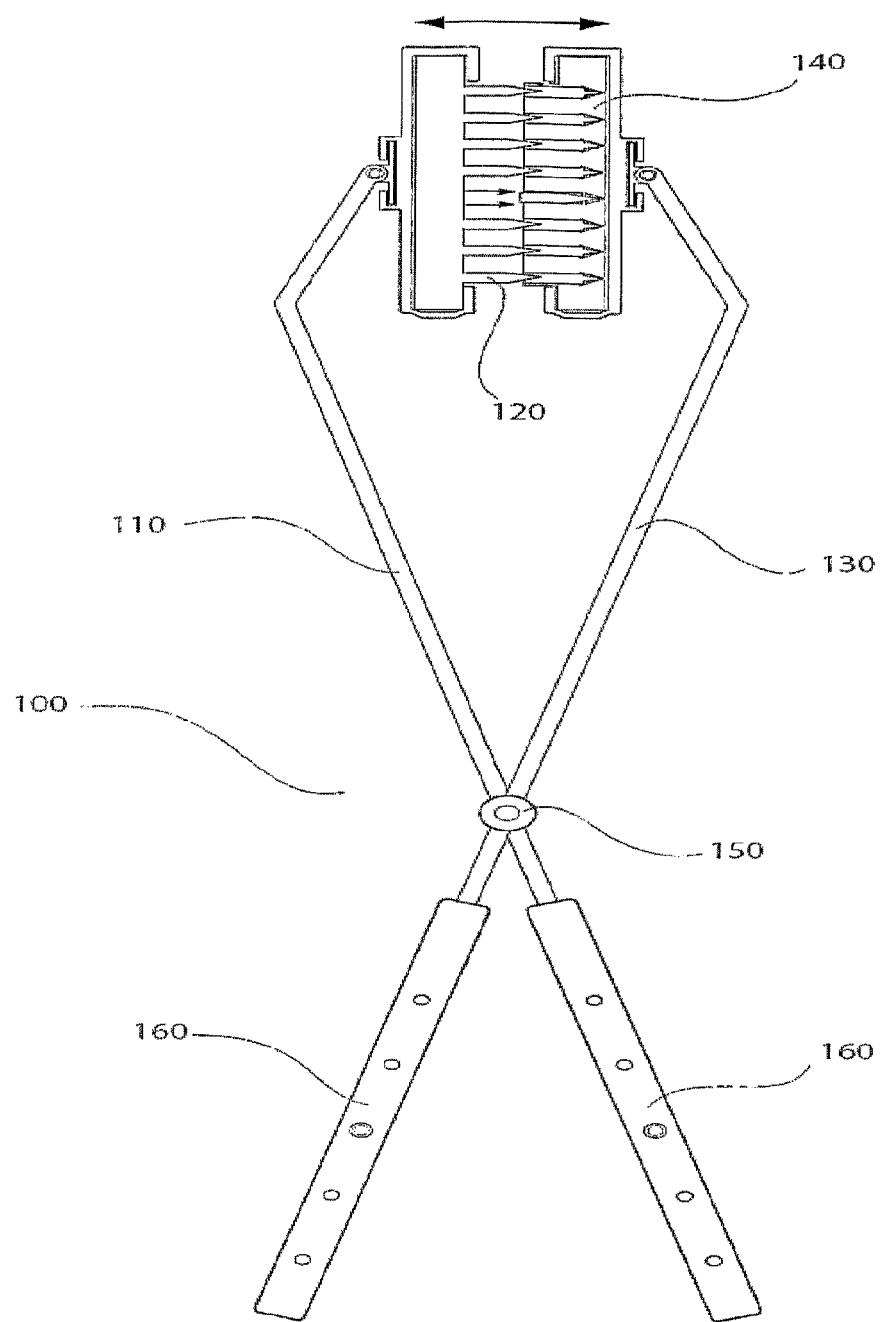
FIG. 1 shows a cross-sectional view of a chemical applicator according to one preferred embodiment of the invention.
Figure 2:
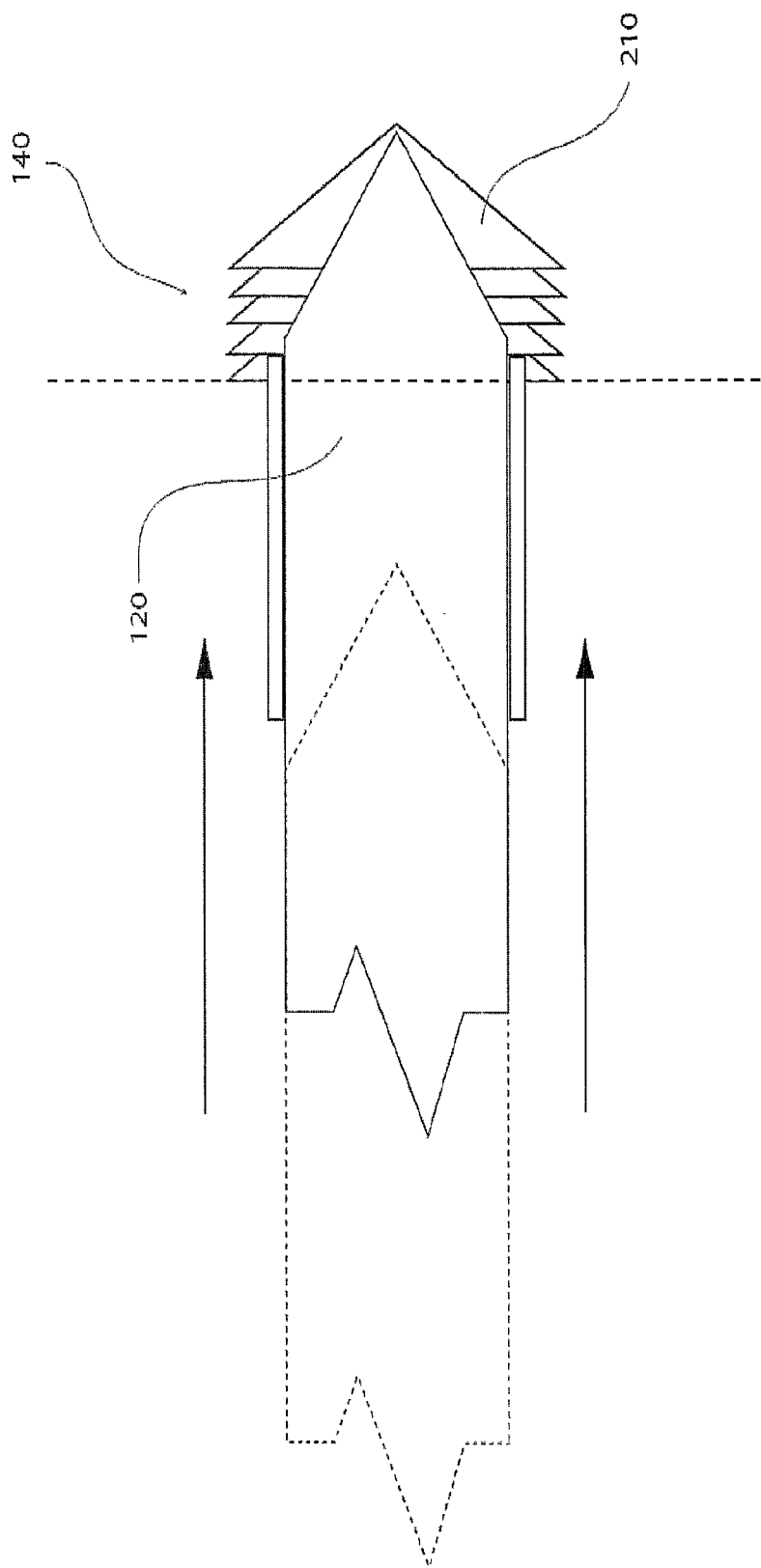
FIG. 2 shows a close-up cross-sectional view of a valve in the chemical reservoir of the chemical applicator shown in FIG. 1.

More preferably, the chemical reservoir 140 comprises one or more valves which are openable in response to the engagement of the one or more piercing elements 120 with the chemical reservoir 140. In a particularly preferred embodiment, as shown in FIG. 2, the chemical reservoir comprises a number of valves 210 which are seated against the internal surface of the chemical reservoir 140 and which are biased to the seated position. When the piercing elements 120 engage with the valves 210, the valves 210 are unseated and pushed back into the interior of the chemical reservoir 140. Once the valve 210 becomes unseated, chemical can emerge from the chemical reservoir 140 and coat the piercing element 120. Therefore the piercing elements 120 emerge from said chemical reservoir 140 via said valves with a chemical coating.

Once the piercing elements 120 are coated, the handles 160 may be separated, thus causing disengagement of the piercing elements 120 from the valves 210 of the chemical reservoir. Once the piercing elements 120 are disengaged, the valves 210 re-seat and thus prevent any further escape of chemical from the chemical reservoir 140. As the handles 160 are further separated, the piercing elements 120 are drawn back through the tissue of the living organism and, accordingly, deliver the chemical carried on the coated piercing elements 120 to the internal tissues of the living organism.

Any chemical remaining on the piercing elements 120 after being drawn through the living organism tissue may be re-applied to the same living organism or a different living organism by placing further living organism tissue in the space between the separated first and second members 110 and 120 and bringing the handles 160 together again. This action would also eventually cause further application of chemical to the piercing elements 120 when they engage with the valves 210 in the chemical reservoir 140, as described above.

The piercing elements 120 are cleansed on reentering said valves into said chemical reservoir 140. Such cleansing is achieved by the wiping of the piecing elements 120 along the valves and/or through wiping a sterilizing substance over said piecing elements 120 on entering said valves into said chemical reservoir 140.

Such cleansing and re-cleansing is achieved by the wiping of the piecing elements as the handle(s) are manipulated by a user to bring the piercing elements 120 and chemical reservoir 140 into, and/or out of, engagement.

Preferably still, the chemical "reservoir" 140 may consist of a "cartridge" which is preloaded with the chemical to release into the target living organism. The distinction between a "reservoir" and a "cartridge" is that a reservoir can be "fed" with the target chemical as well as "drained". The "cartridge" in this arrangement can only be "drained".

In a second form of the invention, the one or more piercing elements are disposed within a chemical reservoir, such that the one or mores piercing elements are normally coated with the chemical; and wherein the one or more piercing elements may be extended outwardly from the chemical reservoir to apply the chemical to a living organism and withdrawn back into the chemical reservoir to effect sealing of the chemical reservoir. A particularly preferred embodiment of this second form of the invention is described with reference to FIG. 3.

In this embodiment, the chemical applicator 300 comprises a chemical reservoir 310 formed from interlocking first 320 and second 330 members. The first 320 and second members 330 are moveable relative to each other to place the chemical reservoir 310 in either an expanded configuration (as shown in panel A) or compressed configuration (as shown in panel B). The first and second members are biased to place the chemical reservoir 310 in an expanded configuration by springs 340.

The chemical reservoir 320 may be compressed into a compressed configuration by applying a force along the longitudinal axis of handle 342. This force causes the first member 320 and second member 330 to move toward each other and causes the springs 340 to compress. The handle 342 is coupled to the second member 330 by a ball joint 344 which enables the handle to be placed at a range of angles relative to the chemical reservoir 310.

The first member 310 comprises a plurality of piercing elements 350 that extend into the interior of the chemical reservoir 310 when the chemical reservoir is in an expanded configuration. In this configuration, the chemical reservoir 310 remains sealed and the piercing elements 350 become coated with chemical held in the chemical reservoir 310. The second member comprises a plurality of apertures 360 placed opposite each of the piercing elements. Each of the apertures 360 comprises a concave rubber gasket 370 to prevent leakage of chemical out of the chemical reservoir 310 through the apertures 360.

When the chemical reservoir 310 is placed into a compressed configuration, the piercing elements 350 penetrate through the concave rubber gaskets 370, which normally seal the chemical reservoir 310. As the piercing elements pass through the rubber gaskets 370, the gaskets wipe the majority of the chemical off the surface of the piercing elements 350. However, the piercing elements 350 comprise a plurality of longitudinal grooves 352. These grooves 352 enable the retention of some chemical on the piercing elements 350 as the piercing elements 350 pass through the gaskets 370. In this configuration, the piercing elements 350 emerge from the chemical reservoir 310 carrying chemical in the grooves 352 thereof, and thus are configured to deliver the chemical to a living organism. Therefore the piercing elements 350 emerge from said chemical reservoir 310 via said gaskets 370 with a chemical coating.

The chemical reservoir 310 may also be disposed within a housing 380. The housing 380 comprises a series of apertures which correspond to the apertures in the chemical reservoir 310, thus enabling the piercing elements 350 to emerge from the chemical reservoir 310 when the chemical reservoir is in the housing 380. In this embodiment, the housing 380 comprises a dorsal aperture 382 which enables connection of the handle 342 to the second member 330. In this way, the chemical reservoir 310 may be compressed into the compressed configuration while the chemical reservoir 310 is retained within the housing 380. In this embodiment, the housing 380 comprises a further aperture which enables the chemical reservoir 310 to be slid into the housing 380. The chemical reservoir 350 is then retained within the housing by one or more ball bearing detents 386.

In use, the device of the second form of the invention is held in an upright position, with the chemical reservoir 310 being proximal to the ground and the handle 342 extending upwardly therefrom. A user may then grip the handle 342 and carry the device to a living organism such as a broadleaf weed or carpetweed. The device may then be positioned over the living organism. Once the device has been positioned over a living organism, the user exerts a force along the length of the handle 342, which, as described above, effects compression of the chemical reservoir 310 and extension of the piercing elements 350, as described above. The extended piercing elements 350 penetrate the tissue of the organism and deliver the chemical thereto. When the force on the handle 342 is released, the springs 340 bias the chemical reservoir 310 into the expanded configuration, which, in turn, causes the piercing elements 350 to retract back into the chemical reservoir 310.

The piercing elements 350 are cleansed on entering said gaskets 370 into said chemical reservoir 310. Further, the piercing elements 350 are re-cleansed on re-entering the chemical reservoir 310. Such cleansing and re-cleansing is achieved by the wiping of the piecing elements along the gaskets 370 and/or through wiping a sterilizing substance over said piecing elements 350 on entering said gaskets into said chemical reservoir 310. The cycle of cleansing and re-cleansing follows the cycle of the user exerting a force along the length of the handle 342, followed by the release of the force causing the piercing elements 350 to retract back into the chemical reservoir 310.

With herbicide use, a preferred embodiment the chemical clasping face can be as small as 4-5 square centimeters incorporating between 9-16 piercing elements. The upper and lower limits1 are not however so limited and could be vastly different, with the optimum size being determined by factors including but not limited to, the chemical type and form and plant type.

Figure 4:
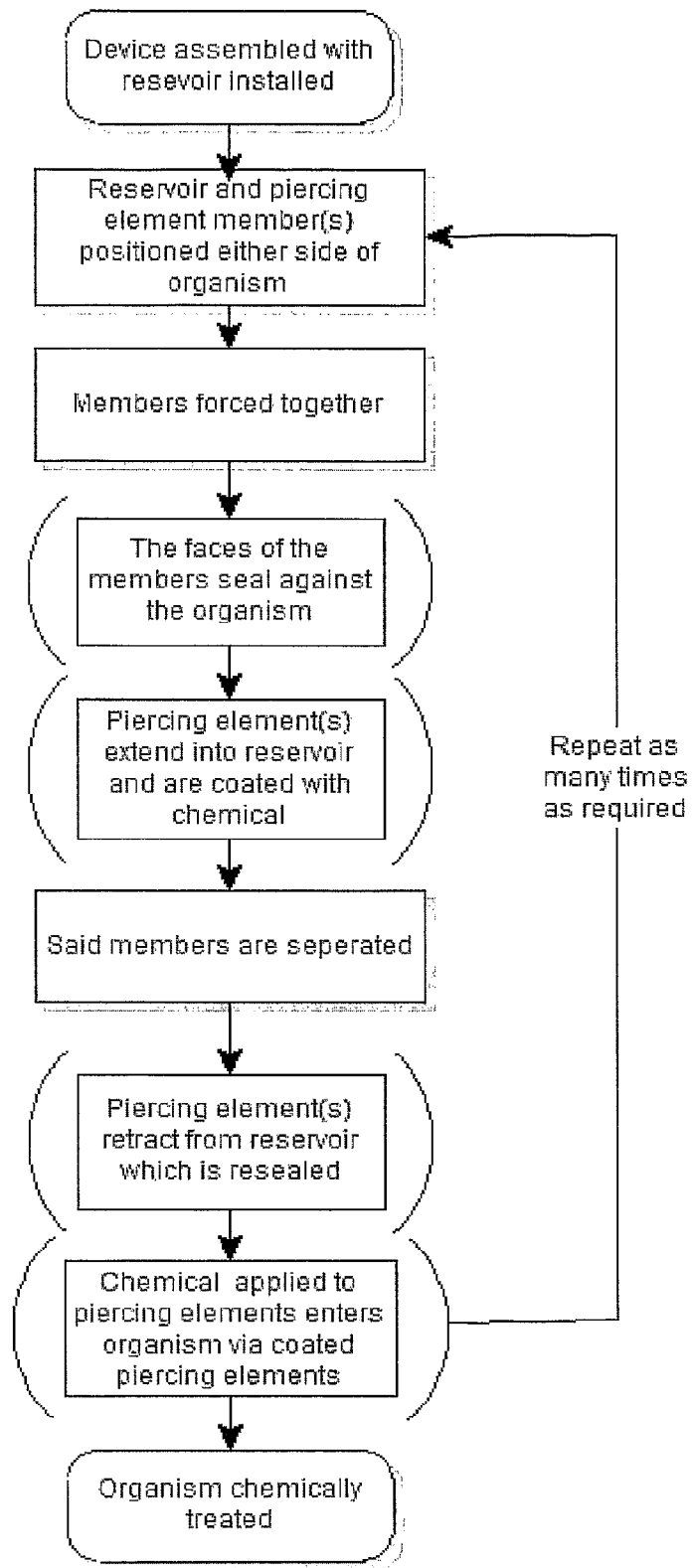
FIG. 4 shows by way of example the flowchart of the first embodiment of the invention shown in FIG. 1.

FIG. 4 shows by way of example the method of applying a chemical to a living organism, including a plant or an animal, with one or more piercing elements and one or more chemical reservoirs, including the steps of:
a) containing the chemical in the chemical reservoirs;
b) disposing the piercing elements within the chemical reservoirs;
c) applying the chemical to the piercing elements within the reservoirs such that the piercing elements are chemically coated;
d) emerge the chemically coated piercing elements from the reservoir;
e) drawing the piercing elements through the animal; and
f) releasing the chemical from the chemically coated, piercing elements into the animal.

The method of delivery, according to the first embodiment of the invention, of the chemical from the piercing elements to a plant, animal or living organism occurs when the organism is interspersed between the members housing the piercing elements and reservoirs. The piercing element which pierces's the animal's surface the members are forced together. Here the faces of the members seal against the organism, whereby the piercing element(s), in the case of a thin plant, extend through the plant into the chemical reservoir, where piercing element(s) are coated with the chemical contained in the reservoir. The members are subsequently separated and the piercing element(s) pass back through organism and the chemical is released from the piercing elements into the organism's body tissue. The cycle can then repeat to re-apply the chemical onto the piercing elements.

A similar cycle can also be repeated when the organism's tissue is too thick to allow the piercing element(s) to pass completely through the tissue. In with the absence of the organism interspersed between the members, when the members are closed the piercing element(s) are coated with the chemical contained in the chemical reservoir. Once the piercing elements are coated and the members are opened and reclosed with an organism, such as an animal or a plant, interspersed between the members, the chemical can be applied via the recoated piercing element(s) insertion into the organism's tissue when the members are forced closed.

The cycle of re-coating the piercing elements can take place once again when the body tissue is too thick to allow the piercing elements and chemical reservoirs to engaged, then the members can be released, allowing the organism to vacate the space between the members. Hence, the piercing elements and reservoir can now engage to allow re-coating of the piercing elements with the chemical.

Figure 3:
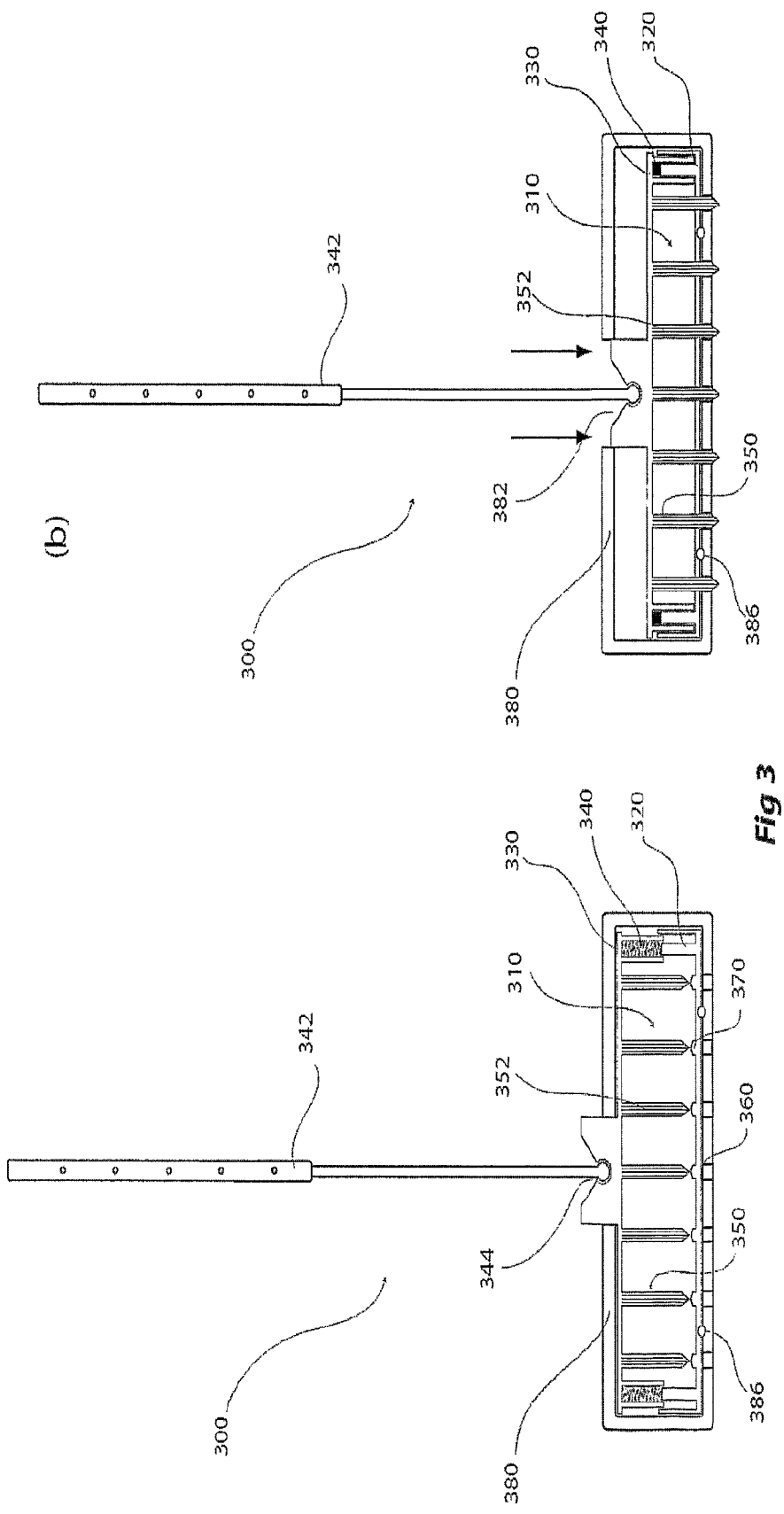
FIG. 3 shows a cross-sectional view of a chemical applicator according to another preferred embodiment of the invention. Panel (a) shows the chemical applicator in an expanded configuration, while panel (b) shows the chemical-applicator in a compressed configuration.
Figure 5:
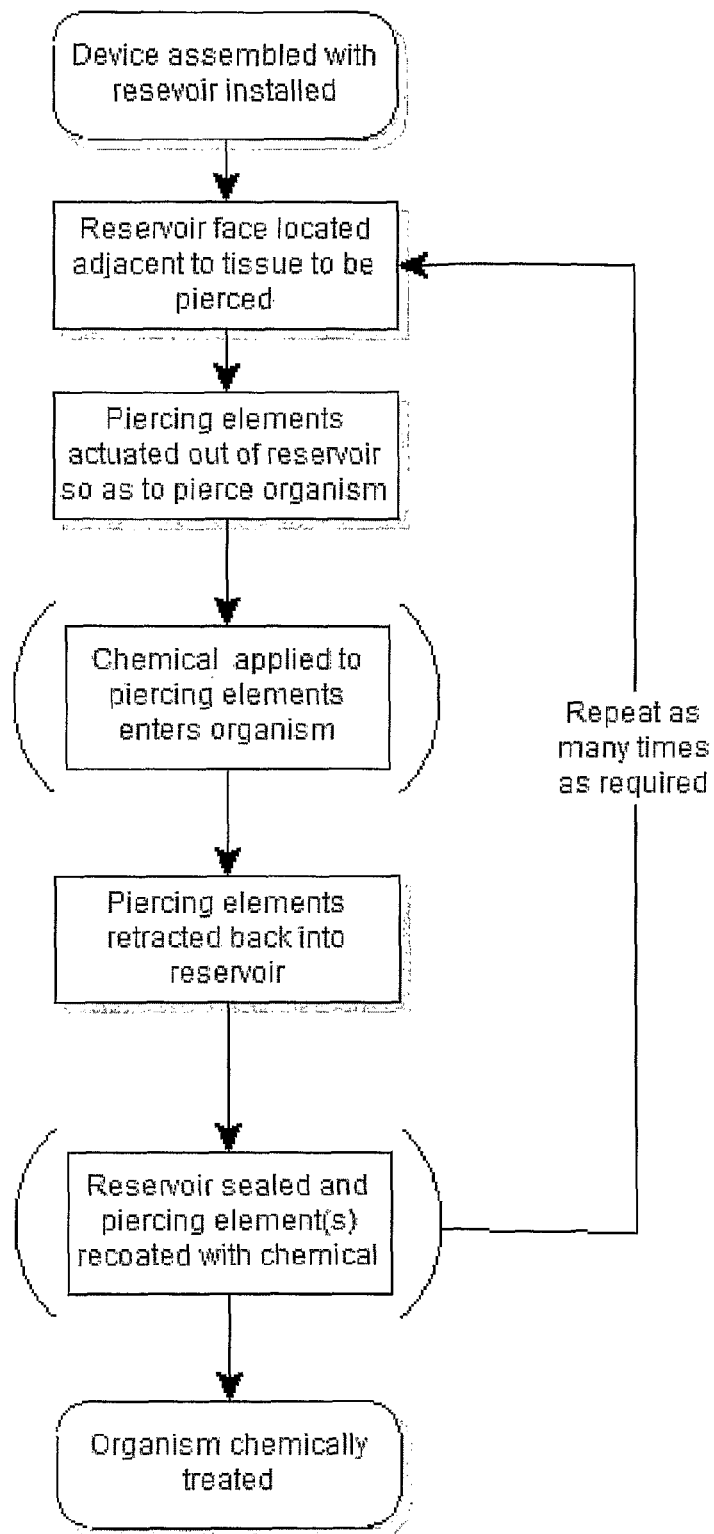
FIG. 5 shows by way of example the flowchart of another embodiment of the invention as shown in FIG. 3.

FIG. 5 shows by way of example the method of applying a chemical, according to the embodiment of the invention shown in FIG. 3, enables the delivery of the chemical to take place when the piercing element, normally biased within the reservoir, being forcibly extended outwards from the reservoir into the animal's contacting surfaces underlying tissue.

As would be appreciated, the present invention encompasses manually-operated embodiments which may be used, for example, in small scale domestic, farming or nursery settings. However, it should also be understood that the present invention also encompasses larger scale, and optionally automated, embodiments which may be used, for example, in market garden, broadacre agriculture farming and aquaculture applications. Furthermore, the invention Nay also be used in conjunction with automated weed sensing systems (for examples, see the publication of Steward and Tian, *Transactions of the ASAE* 42(6): 1897-1910, 1999).

While plant applications have been exemplified in this description, those skilled in the art will recognise that the invention could also administer chemicals not only to plant tissue but also to animal tissue or any living tissue. Those skilled in the art will further appreciate that the invention described herein is susceptible other variations and modifications other than those specifically described. It is to be understood that the invention includes all such variations and modifications. The invention also includes all of the steps or features referred to, or indicated in this specification, individually or collectively, and any and all combinations of any two or more of the steps or features.

Also, it must be noted that, as used herein, the singular forms "a", "an" and "the" include plural aspects unless the context already dictates otherwise. For example "a piercing element" may be a single element or may include a plurality of elements.

Future patent applications may be filed in Australia or overseas on the basis of the present application, for example by claiming priority from the present application, by claiming a divisional status and/or by claiming a continuation status. It is to be understood that the following claims are provided by way of example only, and are not intended to limit the scope of what may be claimed in any such future application. Nor should the claims be considered to limit the understanding of (or exclude other understandings of) the invention or inventions inherent in the present disclosure.

The claims defining the invention are as follows:

1. A device for applying a chemical, said device including:
A. a plurality of piercing elements, each having a first end for piercing a living organism for introducing a chemical into the living organism; and
B. a chemical reservoir for containing said chemical which comprises a body which includes a plurality of valves, each valve corresponding to a piercing element, each valve configured to open in response to the engagement of a corresponding first end of one of the piercing elements and configured to bias closed when the piercing element is disengaged from the valve to prevent further escape of the chemical;
wherein the first end of each of the plurality of: piercing elements is engageable with the chemical reservoir such that said chemical is substantially specifically coated onto the plurality of piercing elements on exit of said reservoir.

2. The device of claim 1 wherein said body includes a cartridge which is preloaded with said chemical.

3. The device of claim 1 wherein said seal is created in said chemical reservoir when one or more said piercing elements sealingly engage with said valves.

4. The device of claim 1 wherein said piercing elements are cleansed on entering said valves into said chemical reservoir.

5. The device of claim 1 wherein said piercing elements emerge from said chemical reservoir via said valves with a chemical coating.

6. The device of claim 1 wherein said piercing elements are re-cleansed on re-entering said valves into said chemical reservoir by application of a sterilizing substance to said piercing elements.

7. The device of claim 1 wherein said piercing elements are raised from a first member which is pivotally attached to a second member which comprises said chemical reservoir.

8. The device of claim 7 wherein said first and said second members includes one or more handles, wherein said handles are actuated to bring the plurality of piercing elements and said chemical reservoir into engagement.

9. The device of claim 1, including an actuator, wherein actuation of said actuator effects extension of said piercing elements and withdrawal from said chemical reservoir.

10. The device of claim 9 wherein said actuator comprises an upright handle and actuation of said actuator comprises the application of force along the longitudinal axis of said handle.

11. The device of claim 9 wherein said chemical reservoir includes one or more gaskets which are openable in response to the engagement of one or more of said piercing elements.

12. The device according to claim 11 wherein a seal is created in said chemical reservoir when one or more of said piercing elements sealingly engage with said gaskets.

13. The device of claim 11 wherein said seal is created in said chemical reservoir when one or more said piercing elements sealingly engage with said gaskets.

14. A method of applying a chemical to a target using a device with a plurality of piercing elements, each having a first end for piercing a target and a chemical reservoir, including the steps of:
   a) disposing said first end of each of said piercing elements through a respective one of a plurality of valves within a chemical reservoir, thereby opening said valves to apply a chemical to said piercing elements within said reservoir such that said piercing elements are chemically coated;
   b) emerging said chemically coated piercing elements from said reservoir whereby said valves are biased closed in response thereto;
   c) drawing said first ends of said piercing elements through said target; and
   d) releasing said chemical from said chemically coated piercing elements into said target;
   such that said delivery of said chemical is undertaken from said piercing elements that are forced upon said target's surface to pierce said target when the plurality of piercing elements, biased to be retained within said reservoir are forcibly extended outwards from said reservoir into said target.

15. The method in claim 14 wherein delivery of said chemical is undertaken when said target is interspersed between said reservoir and said piercing element such that a sealingly engagement is created between the contacting surfaces.

\* \* \* \* \*